United States Patent
Na et al.

(10) Patent No.: US 10,304,578 B2
(45) Date of Patent: May 28, 2019

(54) FUEL PELLET VISUAL INSPECTION DEVICE FOR MANUFACTURING NUCLEAR FUEL ROD

(71) Applicant: KEPCO NUCLEAR FUEL CO., LTD., Daejeon (KR)

(72) Inventors: Tae Hyung Na, Daejeon (KR); Hankyul Koh, Daejeon (KR)

(73) Assignee: KEPCO NUCLEAR FUEL CO., LTD., Daejeon (KR)

(*) Notice: Subject to any disclaimer, the term of this patent is extended or adjusted under 35 U.S.C. 154(b) by 564 days.

(21) Appl. No.: 15/280,218

(22) Filed: Sep. 29, 2016

(65) Prior Publication Data
US 2017/0294243 A1    Oct. 12, 2017

(30) Foreign Application Priority Data
Apr. 7, 2016    (KR) .................. 10-2016-0042912

(51) Int. Cl.
| | | |
|---|---|---|
| *G01B 11/02* | (2006.01) | |
| *G01N 21/01* | (2006.01) | |

(Continued)

(52) U.S. Cl.
CPC .............. *G21C 21/02* (2013.01); *G01B 11/02* (2013.01); *G01N 21/01* (2013.01); *G01N 21/8803* (2013.01); *G01N 21/952* (2013.01); *G01N 21/94* (2013.01)

(58) Field of Classification Search
CPC ........ G21C 21/02; G21C 19/207; G21C 3/33; G21C 3/30; Y10S 294/906; Y10S 294/907; Y10T 29/53039; Y10T 29/53048; Y10T 29/53061; Y10T 29/531; Y10T 29/53539; Y10T 29/49771; B23P 19/04; B23P 19/10; B23P 2700/00; G21Y 2004/401;

(Continued)

(56) References Cited

U.S. PATENT DOCUMENTS

| | | | |
|---|---|---|---|
| 4,193,843 A | | 3/1980 | Womack et al. |
| 4,573,847 A | * | 3/1986 | Howell .................. B65G 57/18 414/609 |

(Continued)

FOREIGN PATENT DOCUMENTS

| | | |
|---|---|---|
| DE | 26 05 962 A1 | 8/1977 |
| JP | 2687311 B2 | 12/1997 |

(Continued)

OTHER PUBLICATIONS

Korean Office Action dated Oct. 13, 2016.
Decision to Grant and Search Report issued Russian Patent Office dated Dec. 20, 2017 (with translation).

*Primary Examiner* — Sarang Afzali
*Assistant Examiner* — Darrell C Ford
(74) *Attorney, Agent, or Firm* — Rabin & Berdo, P.C.

(57) ABSTRACT

A fuel pellet visual inspection device for manufacturing a nuclear fuel rod improves convenience and workability of visual inspection of a plurality of pellets by simultaneously turning over the pellet. The fuel pellet visual inspection device for manufacturing a nuclear fuel rod includes: a rotary shaft; a pair of seats hinged to the hinge shaft, arranged at both sides from the rotary shaft, and seated with a tray thereon; and a dust-collecting unit disposed under the pair of seats and collecting dust scattered from pellets.

9 Claims, 5 Drawing Sheets

(51) Int. Cl.
  *G01N 21/88* (2006.01)
  *G01N 21/94* (2006.01)
  *G21C 21/02* (2006.01)
  *G01N 21/952* (2006.01)

(58) Field of Classification Search
  CPC .............. G21Y 2002/302; G01B 11/02; G01N 21/952; G01N 21/8803; G01N 21/01; G01N 21/94
  USPC ..... 29/407.05, 709, 711, 714, 723, 822, 906
  See application file for complete search history.

(56) References Cited

U.S. PATENT DOCUMENTS

| | | | |
|---|---|---|---|
| 4,687,605 A * | 8/1987 | Cellier | G21C 21/02 252/636 |
| 4,694,571 A * | 9/1987 | Kanai | G03B 42/045 29/709 |
| 5,509,039 A * | 4/1996 | Fogg | G01B 5/02 376/245 |
| 2017/0025195 A1* | 1/2017 | Pineiro Fern Ndez | G21C 17/06 |

FOREIGN PATENT DOCUMENTS

| | | |
|---|---|---|
| KR | 10-2011-0096410 A | 8/2011 |
| KR | 10-2013-0080348 A | 7/2013 |
| KR | 10-1349135 B1 | 1/2014 |
| RU | 2 208 253 C2 | 7/2003 |
| RU | 2 216 801 C2 | 11/2003 |
| RU | 2 240 610 C2 | 11/2004 |

* cited by examiner

FUEL PELLET VISUAL INSPECTION DEVICE FOR MANUFACTURING NUCLEAR FUEL ROD

BACKGROUND OF THE INVENTION

Field of the Invention

The present invention relates to a fuel pellet visual inspection device for manufacturing a nuclear fuel rod and, more particularly, to a fuel pellet visual inspection device for manufacturing a nuclear fuel rod that improves convenience of visual inspection of a plurality of pellets by simultaneously turning over the pellet.

Description of the Related Art

A nuclear reactor is a facility for producing electricity from thermal energy that is produced by nuclear fission by artificially controlling a fission chain reaction of fissile materials.

In general, a light water power reactor uses enriched uranium containing 2~5% uranium-235 of and produces a cylindrical nuclear fuel pellet weighing about 5 g from the uranium to make nuclear fuel for a nuclear reactor.

The formed pellet is dried in a drying furnace, is put into a cladding tube made of a special alloy having good corrosion resistance, and is then made into a nuclear fuel rod therein. Nuclear fuel rods manufactured through this process are bundled in a fuel assembly, loaded into the core of a nuclear reactor, and then burned by a nuclear reaction.

Depending on the types of nuclear fuel, pellets are manufactured in a cylindrical shape having a diameter of around 8 cm and a length of around 10 cm, so about four hundreds of pellets are put in a nuclear fuel rod.

Further, since a fuel assembly is composed of about hundreds of nuclear fuel rods, there is a need for a process of manufacturing nuclear fuel rods by putting tens of hundreds of pellets in a cladding tube in order to manufacture one fuel assembly.

However, pellets may be given different lengths in the manufacturing process and cladding tubes are too longer than unit pellets, so the number of pellets that are put into the cladding tubes is changed due to accumulation of the length differences of the pellets.

Accordingly, the length differences made in the manufacturing process of pellets make it difficult to design an automated process for automatically putting pellets into cladding tubes.

In order to prevent this problem, a method of enabling a worker to visually check pellets in person so that pellets meeting can be put into cladding tubes in accordance with their sizes has been proposed.

That is, as shown in FIG. 1, a plurality of pellets 3 is arranged on a tray 2 having sections 1 divided by a plurality of separators and then a worker visually checks the pellets to examine the sizes of thereof.

A quality examination for determining scratches that may be formed on the pellets 3 in the manufacturing process is also performed, in addition to the examination of the sizes of the pellets 3.

After the upper portions of the pellets 3 exposed on the tray 2 have been examined, the worker turns over and arranges the pellets 3 on the tray 2 and then inspects the lower portions of the pellets 3.

However, as described above, the process of individually turning over and visually checking the pellets 3 on the tray 2 is very inconvenient.

That is, it is not only troublesome, but takes too much time to individually turn over and check the surfaces of a plurality of pellets 3, whereby work efficiency is decreased.

Further, while the pellets 3 are examined, the pellets 3 frequently hit each other and produce dust, but dust disposal is not properly performed and the dust spreads into the air or drops to the floor.

DOCUMENTS OF RELATED ART

[Patent Document 1] Korean Patent No. 10-1349135

SUMMARY OF THE INVENTION

The present invention has been made in an effort to solve the problems and an object of the present invention is to provide a fuel pellet visual inspection device for manufacturing a nuclear fuel rod that can make it easy to visually inspect a plurality of pellets by turning over a tray with the pellets loaded thereon to simultaneously turn over all of the pellets.

Another object of the present invention is to provide a fuel pellet visual inspection device for manufacturing a nuclear fuel rod that can collect dust that is produced while pellets are visually inspected in order to easily dispose of dust.

In order to achieve the above object, according to one aspect of the present invention, there is provided a fuel pellet visual inspection device for manufacturing a nuclear fuel rod, the device including: a rotary shaft; a pair of seats hinged to the hinge shaft, arranged at both sides from the rotary shaft, and seated with a tray thereon; and a dust-collecting unit disposed under the pair of seats and collecting dust scattered from pellets.

The device may further include: a frame; and a pair of support blocks disposed on the frame and supporting both ends of the rotary shaft.

The dust-collecting unit may include: a hopper disposed at an upper portion inside the frame and collecting dust scattered from the pellets; a hopper guide disposed under the hopper; and a dust basket separably combined with the hopper guide and keeping dust therein.

The seats each may include: a bottom corresponding to a tray; and a separation wall vertically formed along an edge of the bottom and preventing the tray on the bottom from separating, and a hinge having a shaft hole through which the rotary shaft is inserted is detachably fastened to a side of each of the seats.

Saddle blocks may be disposed on the frame to support the rear sides of the pair of seats when the seats are unfolded.

The fuel pellet visual inspection device for manufacturing a nuclear fuel rod according to the present invention has the following effects.

First, since it is possible to turn a seat at a side, on which pellets for manufacturing a nuclear fuel rod are loaded, over a seat at another side, it is possible to more conveniently visually inspect the pellets for manufacturing a nuclear fuel rod.

That is, since it is possible to simultaneously turn over a plurality of pellets for manufacturing a nuclear fuel rod on a tray, it is not required to individually turn over and inspect the pellets, so workability can be improved.

Second, since a dust-collecting unit is disposed under seats on which pellets for manufacturing a nuclear fuel rod are inspected, it is possible to easily collect and dispose of dust scattered from the pellets for manufacturing a nuclear fuel rod.

In particular, since a drawer-type dust-collecting basket is provided, it is possible to more easily dispose of dust.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

The terms and words used in the present specification and claims should not be interpreted as being limited to typical meanings or dictionary definitions, but should be interpreted as having meanings and concepts relevant to the technical scope of the present invention based on the rule according to which an inventor can appropriately define the concept of the terms to describe most appropriately the best method he or she knows for carrying out the invention.

Hereinafter, a fuel pellet visual inspection device for manufacturing a nuclear fuel rod according to an embodiment of the present invention is described with reference to FIGS. 2 to 6D.

The fuel pellet visual inspection device for manufacturing a nuclear fuel rod is technically characterized in that it can simultaneously turn over a plurality of pellets for manufacturing a nuclear fuel rod (hereafter, referred to as 'pellets').

Accordingly, it is possible to conveniently visually inspect pellets.

Figure 1:
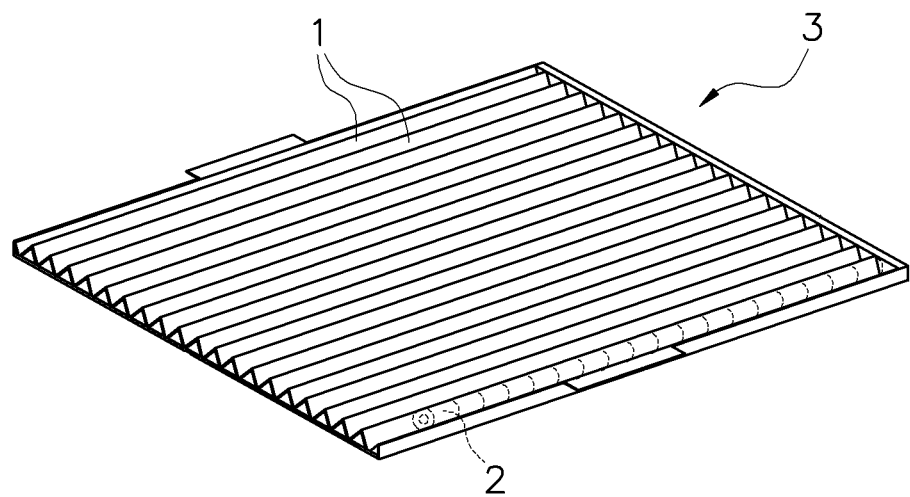
FIG. 1 is a perspective view showing a tray on which pellets for manufacturing a nuclear fuel rod are arranged.
Figure 2:
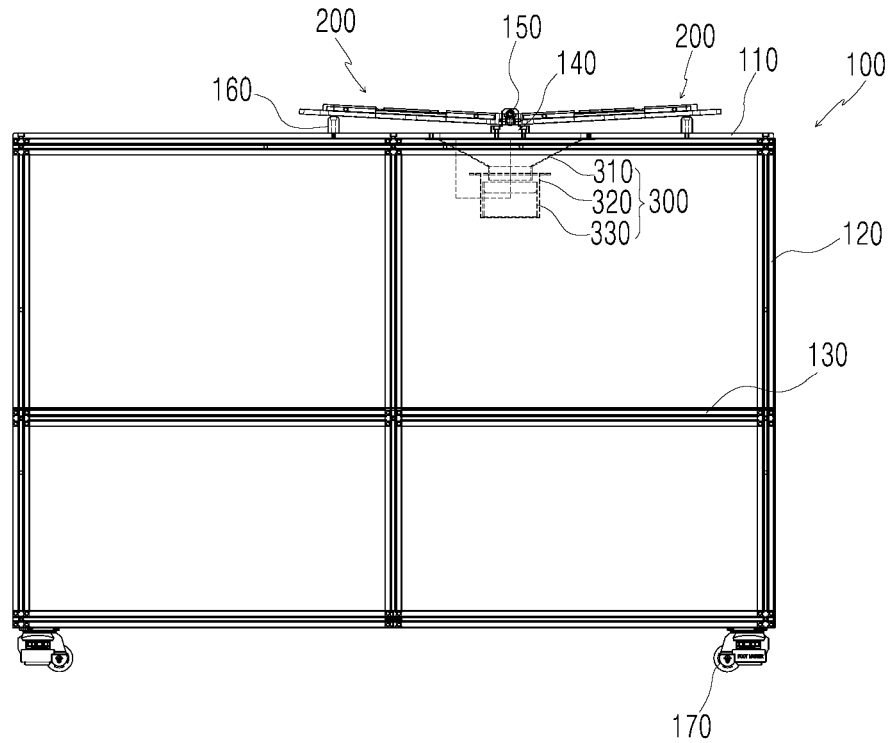
FIG. 2 is a front view showing a fuel pellet visual inspection device for manufacturing a nuclear fuel rod according to an embodiment of the present invention.

A fuel pellet visual inspection device for manufacturing a nuclear fuel rod, as shown in FIG. 2, includes a frame 100, seats 200, and a dust-collecting unit 300.

The frame 100 is a supporting framework where the seat 200 and the dust-collecting unit 300 are mounted, and includes a base plate 110 that is the top thereof, side cover plates 120 that are the sides thereof, and a middle base cover plate 130 connecting the side cover plates 120.

A pair of support block 140 is disposed on a side of the base plate 110.

The support blocks 240 are provided to install a rotary shaft 150, so the rotary shaft 150 is rotatably disposed between the support blocks 140.

A pair of saddle blocks 160 may be disposed on the base plate 110 of the frame 100.

The saddle blocks 160 are provided to support a pair of seats 200 and support the seats 200 such that the seats 200 do not incline downward with respect to the rotary shaft 150.

Wheels 170 may be disposed on the bottom of the frame 110 to easily move.

The seats 200 simultaneously turn over a plurality of pellets arranged on a tray 3 and are disposed over the base plate 110 of the frame 100.

Figure 3:
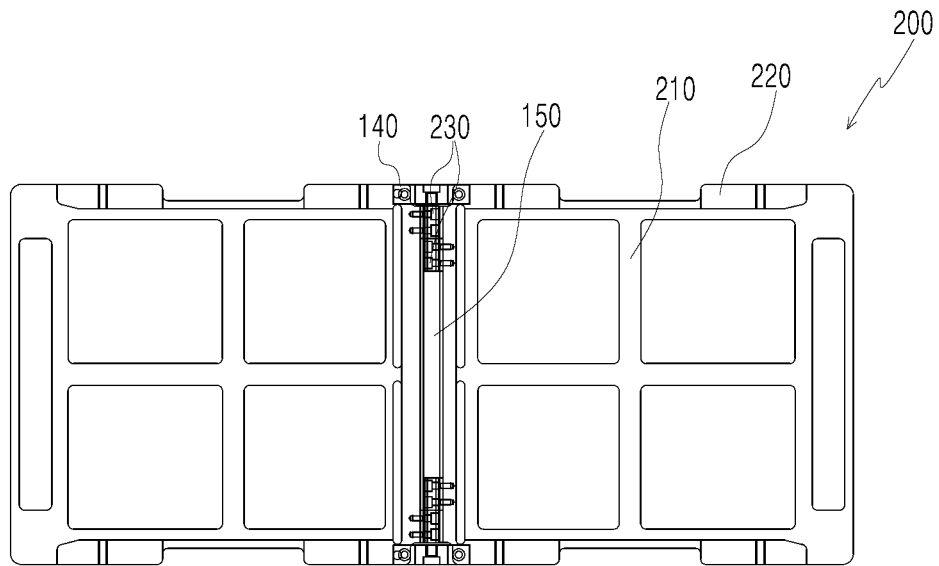
FIG. 3 is a plan view showing a seat of the fuel pellet visual inspection device for manufacturing a nuclear fuel rod according to an embodiment of the present invention.

The seats 200 are arranged in a pair with the rotary shaft 150 therebetween, as shown in FIGS. 2 and 3.

An end of each of the seats 200 is hinged to the rotary shaft 150, so the seats 200 can freely rotate about the rotary shaft 150.

As described above, the seats 200 are supported by the saddle blocks 160.

Figure 4:
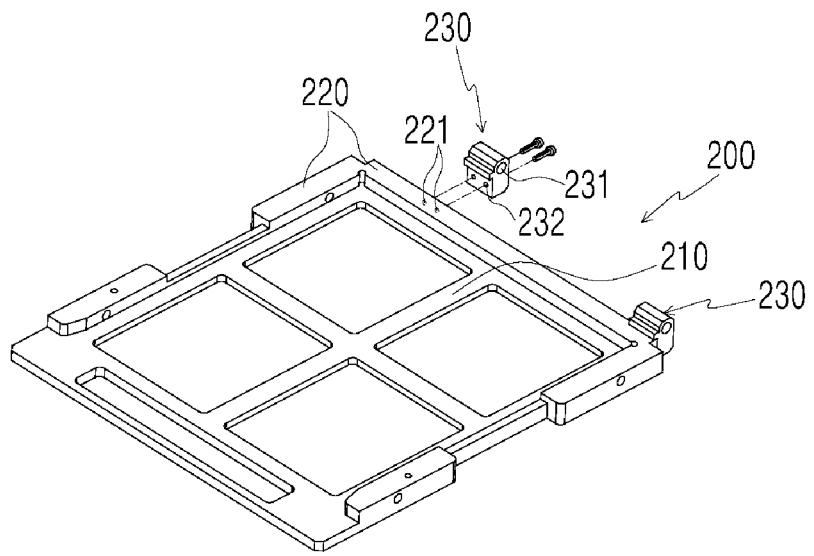
FIG. 4 is an exploded perspective view showing the seat of the fuel pellet visual inspection device for manufacturing a nuclear fuel rod according to an embodiment of the present invention.

The seats 200, as shown in FIG. 4, each have a bottom 210 and a separation wall 220.

The bottom 210 is a part where the tray 3 is placed and may have a size corresponding to the tray 3.

The separation wall 220, which prevents the tray 3 on the bottom 210 from separating from the bottom 210, protrudes upward and is arranged along the edge of the bottom 210.

The separation wall 220 is formed not throughout the edge of the bottom 210, that is, it is not formed at a portion through which the tray 3 is put in and taken out, nor is it formed at a portion where a handle H for holding the seat 220 is formed.

Hinges 230 are disposed on a side of the seat 200.

The hinges 230, which are provided to rotate the seat 200, may be detachably fastened to the sides of the seat 200.

The hinges 230 have a shaft hole 231 through which the rotary shaft 150 for the support blocks 140 is inserted.

The hinges 230 further have fastening holes 232 for bolts to fasten the hinges 230 to the seat 200 and thread-holes 221 are formed at corresponding positions of the separation wall of the seat 200.

According to this configuration, the pair of seats 200 can freely rotate about the rotary shaft 150.

The dust-collecting unit 300 collects dust that is produced in the process of visually inspecting pellets 2 and, as shown in FIG. 2, is fastened to the bottom of the base plate 110.

That is, the dust-collecting unit 300 collects dust dropping from the tray 3 on the seats 200 to dispose of the dust at a specific disposal place.

Figure 5:
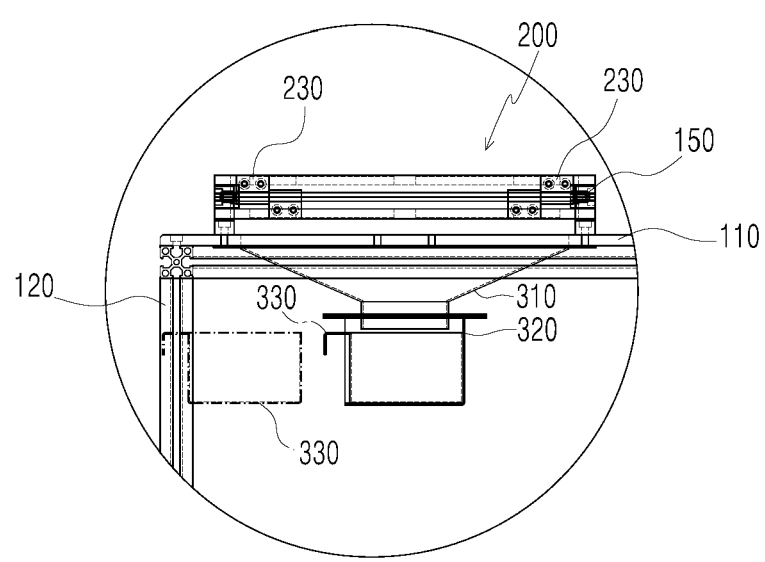
FIG. 5 is an enlarged view showing a dust-collecting unit of the fuel pellet visual inspection device for manufacturing a nuclear fuel rod according to an embodiment of the present invention.

The dust-collecting unit 300, as shown in FIG. 5, includes a hopper 310, a hopper guide 320, and a dust basket 330.

The hopper 310, which is an entrance through which dust dropping from the seats 200 enters the basket 330, is fastened to the bottom of the base plate 110.

The rotary shaft 150 may be positioned on the center line of the hopper 310.

The hopper guide 320, which guides the dust dropping through the hopper 310 into the basket 330, is disposed under the hopper 310.

An entrance (not shown) for the dust basket 330 is formed at a side of the hopper guide 320.

The dust basket 330, which provides a space for collecting the dust dropping through the hopper guide 320, is separably combined with the hopper guide 320.

The dust basket 330 may be formed like a drawer and is put in and taken out through the entrance formed at the hopper guide 320.

When a predetermined amount of dust is collected in the dust basket 330, it is possible to take out the dust basket 330 from the hopper guide 320 to dispose of the dust at a specific disposal space.

Hereinafter, the operation of the fuel pellet visual inspection device for manufacturing a nuclear fuel rod having the configuration described above is described.

Figure 6A:
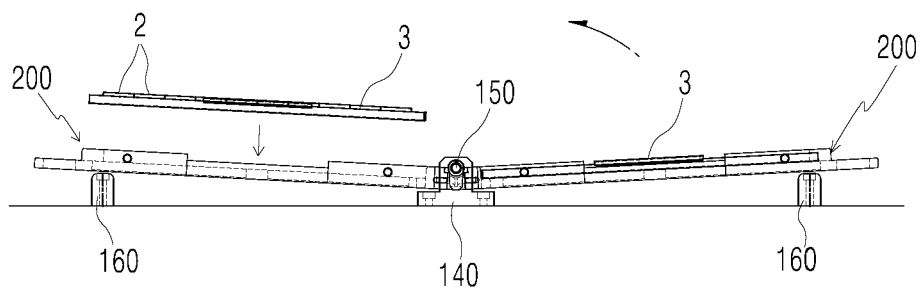
FIGS. 6A to 6D are views showing a process of turning over pellets from one side to another side using the fuel pellet visual inspection device for manufacturing a nuclear fuel rod according to an embodiment of the present invention.

As shown in FIG. 6A, the pair of seats 200 are unfolded to both sides from the rotary shaft 150.

The seats 200 are supported on the saddle blocks 160, in which they may be inclined upward.

Next, trays 3 are put on the bottoms 210 of the seats 200.

Pellets 2 are arranged on the tray 3 on one of the seats 200.

For the convenience of description, it is assumed that the tray 3 where the pellets are arranged 2 is the tray 3 at the left side in the figure (FIG. 6A).

Thereafter, a worker visually inspects the pellets 2 on the tray 3.

The pellets 2 have a cylindrical shape and laid down on the tray 3, so only the upper portions, that is, only the halves of the pellets 2 are visually inspected.

Figure 6B:
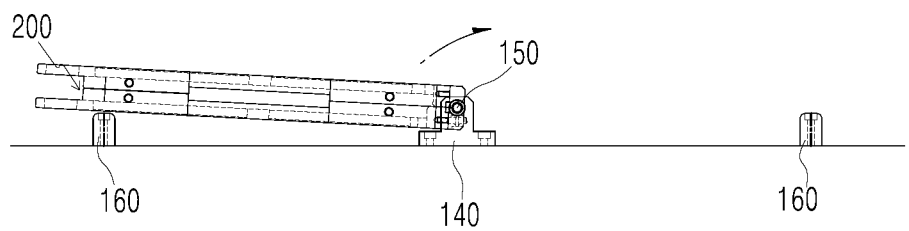

After the exposed halves of the pellets 2 are visually inspected, the left seat 200 is turned over the right seat 200, as shown in FIG. 6B.

Accordingly, the pellets 2 are covered with the tray 3 on the right seat 200.

Figure 6C:
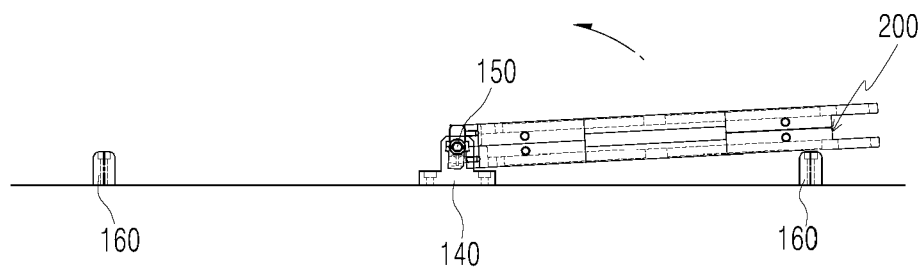

Next, as shown in FIG. 6C, the overlapping seats 200 are turned to the right, thereby turning over the pellets 2.

Accordingly, the pellets 2 are turned over and moved to the tray 3 on the right seat 200.

Figure 6D:
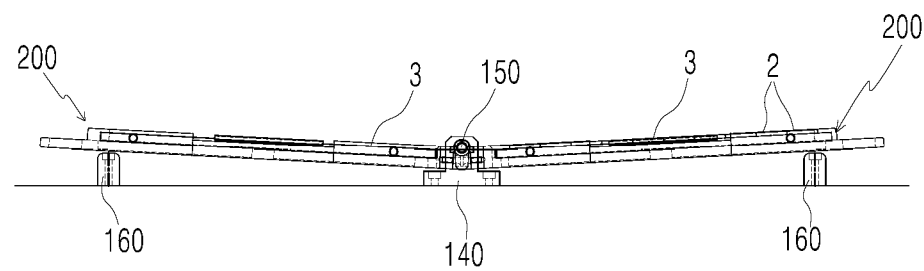

Next, as shown in FIG. 6D, the left seat 200 is turned and unfolded.

It will be understood that the exposed portions of the pellets 2 turned over on the right seat 200 are the lower portions that were not exposed in the previous inspection.

Thereafter, the worker visually inspects the now-exposed lower portions of the pellets 2 on the tray 3 on the right seat 200.

After the visual inspection is finished, the trays 3 are moved to a specific place, whereby a process of visual inspection is finished.

On the other hand, the worker takes out the dust basket 330 with dust produced during the inspection therein through the entrance of the hopper guide 320 and disposes of the dust at a predetermined disposal place.

The fuel pellet visual inspection device for manufacturing a nuclear fuel rod of the present invention described above is technically characterized by making it possible to simultaneously turn over a plurality of pellets.

Accordingly, it is possible to conveniently and efficiently visually inspect pellets.

Further, since it is possible to collect and dispose of dust scattered from pellets using a dust-collecting unit, it is possible conveniently dispose of dust.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A fuel pellet visual inspection device for manufacturing a nuclear fuel rod, the device comprising:
    a rotary shaft;
    a first hinge and a second hinge having a shaft hole, respectively, through which the rotary shaft is inserted;
    a first seat detachably fastened to the first hinge and a second seat detachably fastened to the second hinge, the first and second seats being rotatable on the rotary shaft by the first and second hinges, respectively;
    a first tray placed on one of the first and second seats, wherein pellets are configured to be arranged on the first tray; and
    a dust-collecting unit disposed under the first and second seats and configured to collect dust scattered from the pellets.

2. The device of claim 1, further comprising:
    a frame; and
    a pair of support blocks disposed on the frame and supporting both ends of the rotary shaft.

3. The device of claim 2, wherein the dust-collecting unit includes:
    a hopper disposed at an upper portion inside the frame;
    a hopper guide disposed under the hopper; and
    a dust basket separably combined with the hopper guide.

4. The device of claim 3, wherein each of the first and second seats includes:
    a bottom corresponding to the first tray; and
    a separation wall vertically formed along an edge of the bottom and preventing the first tray on the bottom from separating.

5. The device of claim 3, wherein saddle blocks are disposed on the frame to support respective rear sides of the first and second seats when the first and second seats are unfolded.

6. The device of claim 2, further comprising saddle blocks disposed on the frame to support respective rear sides of the first and second seats when the first and second seats are unfolded.

7. The device of claim 2, wherein each of the first and second seats includes:
    a bottom corresponding to the first tray; and
    a separation wall vertically formed along an edge of the bottom and preventing the first tray on the bottom from separating.

8. The device of claim 1, wherein each of the first and second seats includes:
    a bottom corresponding to the first tray; and
    a separation wall vertically formed along an edge of the bottom and preventing the first tray on the bottom from separating.

9. The device of claim 1, further comprising:
    a second tray placed on the other one of the first and second seats.

* * * * *